(12) United States Patent
Dawis et al.

(10) Patent No.: US 7,833,288 B2
(45) Date of Patent: Nov. 16, 2010

(54) COMPOSITIONS FOR TREATING KERATIN AND METHODS OF USE

(75) Inventors: Suzanne Dawis, Florence, KY (US); Jordan M. Cordeiro, Liberty Township, OH (US); Elisabeth M. Cox, Cincinnati, OH (US); Kevin Phifer, Cincinnati, OH (US); Maggie Cantwell, Cincinnati, OH (US)

(73) Assignee: Kao Brands Company, Cincinnati, OH (US)

( * ) Notice: Subject to any disclaimer, the term of this patent is extended or adjusted under 35 U.S.C. 154(b) by 85 days.

(21) Appl. No.: 12/241,809

(22) Filed: Sep. 30, 2008

(65) Prior Publication Data

US 2009/0094763 A1  Apr. 16, 2009

Related U.S. Application Data

(63) Continuation-in-part of application No. 11/871,500, filed on Oct. 12, 2007.

(51) Int. Cl.
*D06M 19/00* (2006.01)
*A61K 8/00* (2006.01)

(52) U.S. Cl. .............................. 8/94.1 R; 8/463; 8/499; 8/500; 8/594; 424/70.14

(58) Field of Classification Search ................ 8/94.1 R, 8/463, 499, 500, 594; 424/70.14
See application file for complete search history.

(56) References Cited

U.S. PATENT DOCUMENTS

| | | | |
|---|---|---|---|
| 5,643,341 A | 7/1997 | Hirsch et al. | |
| 5,690,921 A | 11/1997 | Lang et al. | |
| 5,843,193 A | 12/1998 | Hawkins et al. | |
| 6,908,491 B2 | 6/2005 | Fischer et al. | |
| 2004/0247550 A1* | 12/2004 | Asari et al. | 424/70.12 |
| 2005/0058618 A1* | 3/2005 | Evans et al. | 424/70.14 |
| 2005/0226838 A1* | 10/2005 | Krause et al. | 424/70.13 |
| 2005/0260146 A1 | 11/2005 | Blin | |
| 2007/0006399 A1* | 1/2007 | Carrascal et al. | 8/409 |

FOREIGN PATENT DOCUMENTS

| | | |
|---|---|---|
| EP | 0970685 A1 | 1/2000 |
| JP | 60152408 | 8/1985 |
| WO | 02102350 A2 | 12/2002 |
| WO | 2004103335 A1 | 12/2004 |

OTHER PUBLICATIONS

Gomes, et al., "The use of silicones in hair colorant formulations," Dow Corning Corporation, 2000.

(Continued)

*Primary Examiner*—Eisa B Elhilo
(74) *Attorney, Agent, or Firm*—Morris, Manning & Martin, LLP; Christopher W. Raimund

(57) ABSTRACT

The disclosure relates to a method for applying to skin, an aqueous composition comprising one or more acid direct dyes and an organic solvent, wherein the composition has a pH of 2-6 and wherein the composition is free of anionic surfactants. The method also comprises applying the aqueous composition to the skin by spraying and further comprises rinsing the composition from skin with water.

15 Claims, 1 Drawing Sheet

OTHER PUBLICATIONS

"Dow Corning® 1501 Fluid," Product Information, Personal Care, Dow Corning Corporation.

ColorStay® Permanent Cream-Gel Haircolor, ©1999 Revlon Consumer Products Corporation, 1 pages.

Silver Edge Beauty Supply, MultiBEAUTY.com, A Division of Silver Edge Co., http://mall.weborder.com, pp. 1-6.

ColorPlus, Tricostyle.com, www.tricostyle.com/HTML/colorPlus.html, 4 pages, (1942).

* cited by examiner

COMPOSITIONS FOR TREATING KERATIN AND METHODS OF USE

This application is a continuation-in-part of U.S. patent application Ser. No. 11/871,500, filed on Oct. 12, 2007, pending, which is incorporated by reference herein in its entirety.

BACKGROUND

1. Technical Field

This application relates generally to compositions for treating keratin and methods of use, and, in particular, to compositions comprising one or more acid direct dyes and to methods of applying these compositions to hair or skin to impart color thereto.

2. Background of the Technology

It is well appreciated that individuals often wish to cosmetically alter the coloring of their hair by various known hair coloring treatments and that many individuals change their own hair color to their favorite hair color using currently available hair dye compositions. In particular, oxidative dye compositions are commonly used because such compositions simultaneously decolorize and dye hair, thus widening the degree of freedom of hair color. Thus, individuals having comparatively dark hair are able to use such products. Moreover, the products provide a greater number of color variations.

Use of oxidative dye compositions to treat hair is typically expensive and can be time consuming as well. In addition, the chemicals employed in these treatments can be caustic and somewhat damaging to the hair. Their frequent use is not preferred, and rather they are generally used at intervals of at least about one month. It is unavoidable that the color of hair dyed with oxidative dye compositions gradually fades during this one month owing to the influence of washing with shampoo, sweat, ultraviolet rays from sunshine and the like. The gradual fading of color results in a gradual reduction in the feeling of satisfaction generally felt immediately after dyeing.

Thus, individuals who have had their hair color-treated are often desirous of prolonging the effects of treatment for as long as possible and otherwise wish to keep their hair in as healthy a state as possible between visits to the colorist. One way of prolonging the freshness of a hair coloring treatment and to otherwise preserve the condition of the hair is to use hair color maintenance shampoos, conditioners, rinses, mousses, gels, sprays and the like. Examples of such hair color maintenance products include AVEDA™ shampoos and conditioners; TRICOL™ Color Plus™ products; ARTec Color Enhancing shampoos and conditioners; LOGICS™ Color Refresher™; and UTENA™ Cha Charl™. Such hair color maintenance products are typically formulated with a degree of coloring, so as to assist an individual in an attempt to prolong the duration of the coloring treatment. These products have a number of drawbacks, however. For example, such products require daily use in order to maintain hair color. Furthermore, such products are low in hair dyeing power, thus being insufficient for revitalizing fading color.

Methods for maintaining hair color are also disclosed in U.S. Pat. No. 5,643,341. In addition, a color refreshing rinse has been sold under the name ROUX® Fancifull®.

There still exists a need for improved color revitalizing products for hair that has been previously treated with an oxidative dye composition to supply color to the hair that has been lost by washing or shampooing. In addition, since untreated hair also fades when exposed to sunlight, shampooing and styling tools such as curling irons and dryers, there also exists a need for improved products which can be used on hair that has not been previously treated with an oxidative dye composition to impart color thereto.

SUMMARY

According to a first embodiment, a composition is provided which comprises:
one or more acid direct dyes;
an organic solvent; and
an oil phase;
wherein the oil phase content of the composition is 5 percent by weight or less and wherein the composition has a pH of 2-6.

According to a second embodiment, a method is provided which comprises:
applying a composition as set forth above to hair;
allowing the composition to remain on the hair; and
subsequently rinsing the composition from the hair with water.

According to a third embodiment, a method is provided which comprises applying an aqueous composition comprising one or more acid direct dyes and an organic solvent to skin, wherein the composition has a pH of 2-6.

DETAILED DESCRIPTION

Figure 1:
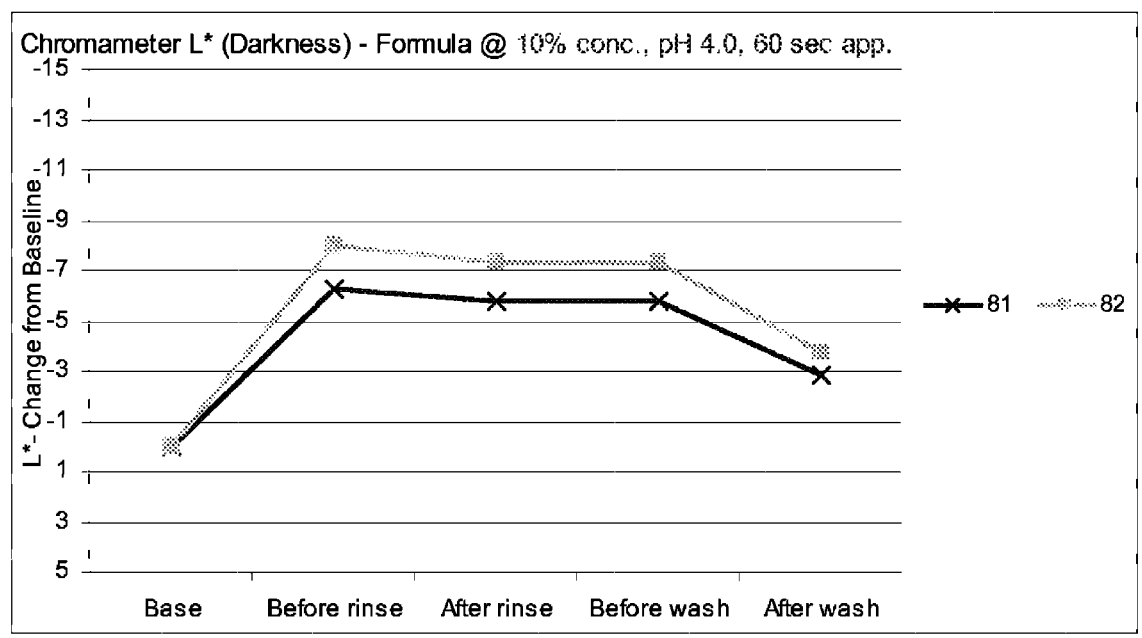
FIG. 1 is a graph showing the change in baseline skin tone achieved by applying a composition as described herein to the skin wherein the change in skin tone is shown before rinsing, after rinsing, before washing and after washing.

A system and method for color-revitalizing hair is disclosed in U.S. Pat. No. 6,908,491 B2, which is incorporated by reference herein in its entirety. The compositions disclosed in this patent include at least one direct dye (e.g., an acid direct dye). The compositions disclosed in this patent also include, in addition to the direct dyes, propylene carbonate, ethanol, xanthan gum, a polyether modified silicone, lactic acid, sodium hydroxide, a perfume base and water. These compositions can be applied to hair previously dyed with an oxidative hair dye composition.

Various formulations designed to restore color to hair are currently being sold under the "John Frieda Luminous Color Glaze". These formulations have a base formula as set forth in the following table:

| Material Description | % Weight/% Weight |
| --- | --- |
| Propylene Carbonate | 15.0000 |
| Xanthan Gum | 1.5000 |
| Ethanol | 4.9500-5.0000 |
| Sodium Hydroxide | 0.1000 |
| Citric Acid | 2.5550 |
| Methylchloroisothiazolinone (and) Methylisothiazolinone | 0.0700 |
| PEG-12 Dimethicone | 2.4000 |
| Hydrogenated Polydecene | 2.0000 |
| Oleyl Alcohol | 1.0000 |
| Dimethicone | 2.6400 |
| Dimethiconol | 0.3600 |
| Deionized Water | QS to 100% |
| Frangrance, Extracts and Pigments | Less than 2% |

These products also include various combinations of acid dyes. For example, the "Luminous Glaze" products for blonde and brunette hair include combinations of Orange 4, Yellow 10, and External Violet 2 whereas the products for red hair include either a combination of Orange 4, Red 33, and External Violet 2 or a combination of Orange 4 and Red 33. These products are oil-in-water dispersions having an oil phase content of about 8.4 percent by weight based on the total weight of the composition. The oil phase of these composition includes Hydrogenated Polydecene, Oleyl Alcohol, PEG-12 Dimethicone, Dimethicone and Dimethiconol.

The compositions described herein have an oil phase content of 5 percent by weight or less based on the total weight of the composition. These compositions can be applied to either undyed hair or to previously dyed hair (e.g., to hair previously treated with an oxidative dye composition). These compositions include an organic solvent and an acid direct dye. Examples of the acid direct dye include Yellow No. 203 (D & C Yellow No. 10, Color Index (CI) given as (CI 47005)), Orange No. 205 (D & C Orange No. 4 (CI 15510)), Red No. 227 (D & C Red No. 33 (CI (Color index) 17200)), Violet No. 401 (Ext. D & C Violet No. 2 (CI 607301)) and Black No. 401 (CI 20470). The compositions can include an acid direct dye or a combination of acid direct dyes selected from the group consisting of Yellow No. 10, Orange No. 4, External Violet No. 2, Red No. 33 and combinations thereof. For example, compositions for blonde and brunette hair can include combinations of Orange 4, Yellow 10 and External Violet 2 and compositions for red hair can include either a combination of Orange 4, Red 33, and External Violet 2 or a combination of Orange 4 and Red 3.

According to a one embodiment, the composition comprises one or more acid direct dyes, an organic solvent and a cyclic dimethyl polysiloxane compound. According to a further embodiment, the composition comprises one or more acid direct dyes, one or more carboxylic acid compounds, and an organic solvent, wherein the one or more carboxylic acid compounds includes malic acid.

Examples of the organic solvent include benzyl alcohol, 2-benzyloxyethanol, propylene carbonate, gamma-butyrolactone and N-methylpyrrolidone. An exemplary solvent is propylene carbonate which has an empirical formula of $C_4H_6O_3$ and a chemical structure as set forth below:

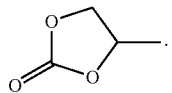

The compositions can also comprise one or more preservatives. Exemplary preservatives include methylchloroisothiazolinone, methylisothiazolinone and combinations thereof.

A thickener may also be added to the composition to prevent running and the like, thereby facilitating its application to hair. An exemplary thickener is xanthan gum.

The compositions may also include a solubilizing agent for the organic solvent in water. Ethanol, propylene glycol or the like can be used as the solubilizing agent.

The compositions have an acidic pH. For example, the compositions can have a pH of 2 to 6, particularly a pH of 2 to 5, and more particularly a pH of 2 to 4. The adjustment of the pH may be conducted in accordance with any known method.

The compositions may also include an inorganic base such as sodium hydroxide as well as an organic carboxylic acid. Exemplary organic carboxylic acids include citric acid, malic acid and combinations thereof.

The composition can further comprise a component selected from the group consisting of: *Theobromo Cacao* Extract; *Camellia Sinensis* Leaf Extract; *Fragaria Vesca* (Strawberry) Fruit Extract; *Zingiber Officinale* Leaf Extract; *Prunus Domestica* Fruit; *Punic Granatum* Leaf Extract; *Helianthus Annuus* (Sunflower) Seed Extract; Citrus *Medica Limonum* (Lemon) Peel Extract; *Chamomilla Recutita* (*Matricaria*) Flower Extract; *Helianthus Annuus* (Sunflower) Seed Oil; *Triticum Vulgare* (Wheat) Germ Oil; and *Triticum Vulgare* (Wheat) Germ Extract. Compositions formulated for brown hair can include *Theobromo Cacao* Extract, *Camellia Sinensis* Leaf Extract or combinations thereof. Compositions formulated for red hair can include *Fragaria Vesca* (Strawberry) Fruit Extract (and) *Zingiber Officinale* Leaf Extract, *Prunus Domestica* Fruit (and) *Punic Granatum* Leaf Extract or combinations thereof. Compositions formulated for blonde hair can include *Helianthus Annuus* (Sunflower) Seed Extract; Citrus *Medica Limonum* (Lemon) Peel Extract; *Chamomilla Recutita* (*Matricaria*) Flower Extract, *Helianthus Annuus* (Sunflower) Seed Oil, *Triticum Vulgare* (Wheat) Germ Extract, *Triticum Vulgare* (Wheat) Germ Oil and combinations thereof.

Compositions formulated for brown hair can also include pearl powder. Compositions formulated for blonde hair can also include panthenol, tocopheryl acetate and/or hydroxypropyltrimonium honey. Compositions formulated for red hair can also include tocopheryl acetate, magnesium ascorbyl palmitate and retinyl palmitate.

The compositions can also include mica, iron oxides, titanium oxide and combinations thereof. For example, compositions formulated for blonde hair can include mica and titanium dioxide. Compositions formulated for red hair can include iron oxide and mica and, optionally, titanium dioxide. Compositions formulated for brown hair can include iron oxide and mica and titanium dioxide.

The compositions can also include a fragrance.

According to one embodiment, the composition is in the form of an oil-in-water emulsion having an oil phase content of 5% by weight or less based on the total weight of the composition. According to a further embodiment, the composition is in the form of an oil-in-water dispersion having an oil phase content of 3% by weight or less or from 2.0 to 3.0 percent by weight based on the total weight of the composition.

According to a further embodiment, a composition is provided which comprises, as an oil phase, 2.5 percent by weight based on the total weight of the composition of a silicone fluid. The silicone fluid can be a combination of cyclopentasiloxane (and) dimethiconol. Compositions comprising 2.5 percent by weight based on the total weight of the composition of a combination of cyclopentasiloxane and dimethiconol were evaluated and were surprisingly found to impart satisfactory levels of hair conditioning without producing a greasy feel.

When a composition comprising an acid direct dye and/or an organic solvent and having an acidic pH is used as the color-revitalizing composition, the dullness of hair is improved, and a feeling of transparency, luster, shine, structure, body, deep shade and manageability is imparted to the hair.

The color-revitalizing compositions used in the present invention may be prepared in the form of a gel, a cream, a liquid, a foam or the like and may also be provided in the form of an aerosol.

Methods for applying the compositions include a method in which either dry hair or wetted hair is coated with an amount of the composition sufficient to evenly spread the composition throughout the hair. The composition is then left to stand for a period of time (e.g., 3 to 45 minutes), rinsed out with warm water, optionally shampooed and rinsed, and then dried. An alternative method is one in which hair that has been shampooed and wiped with a towel is coated with an amount of the composition sufficient to evenly spread the composition throughout the hair, left to stand for 3 to 45 minutes, rinsed out with warm water, optionally shampooed and rinsed, and then dried. The hair may also be conditioned after shampooing and before or after treatment with the composition.

The composition and method of the invention is simple and does not require large amounts of time to carry out. An example of a method of applying the composition to hair includes:
uniformly apply the composition to damp hair;
leave in for 3 minutes;
rinse out; and
proceed with normal hair care routine.

The composition can be applied to the hair using gloves to prevent staining of the user's skin. The compositions can be applied weekly or more or less frequently as necessary to maintain beautiful hair color.

If desired, one can preview the results prior to use by doing a simple strand test as follows:
1) dampen an underneath section of hair (½ to 1 inch);
2) apply the color revitalization composition (about a dime size) and massage in thoroughly;
3) after approximately 3 to 10 minutes, then rinse;
4) dry and inspect hair to confirm the color restoration.

Another example of a protocol for applying the color revitalizing composition of the invention includes:
dampen hair (i.e., such that the hair is not soaking wet);
using gloves, squeeze about a half-dollar sized amount into palm of hand (about 2 tablespoons);
adjust the amount used as necessary for length of type of hair;
massage into hair;
rub in until all hair is uniformly covered;
leave in hair for 10 minutes;
shampoo the composition out of the hair; and
rinse until the rinse water is free from coloration.

The user can then proceed with a normal hair care and styling routine.

The compositions can be applied about one to three times a week to maintain a beautiful, shiny, fresh-colored look. More frequent use will increase the coloring effect, if desired.

Specific formulations are set forth in the following table. Formulations I-VI include various combinations of acid dyes which can be applied to hair to achieve a desired coloring effect. In particular, formulation I imparts a "chestnut" color to the hair of a user, formulation II imparts an "amber" color to the hair of a user, formulations III and IV impart a red color to the hair of a user, formulation V imparts a "platinum" color to the hair of a user, and formulation VI imparts a "honey" color to the hair of a user.

| | Shade | | | | | |
|---|---|---|---|---|---|---|
| | I | II | III | IV | V | VI |
| | Chestnut | Amber | Vivid Red | Richer Red | Platinum | Honey |
| Material Description | % Wt./Wt. | % Wt./Wt. | % Wt./Wt. | % Wt./Wt. | % Wt./Wt. | % Wt./Wt. |
| WATER | 72.7621550 | 72.7855650 | 72.6023600 | 72.5944600 | 72.8365244 | 72.8314244 |
| PROPYLENE CARBONATE | 15.0000000 | 15.0000000 | 15.0000000 | 15.0000000 | 15.0000000 | 15.0000000 |
| ALCOHOL DENAT. | 4.9500000 | 4.9500000 | 4.9500000 | 4.9500000 | 4.9500000 | 4.9500000 |
| CITRIC ACID | 2.5550000 | 2.5550000 | 2.5550000 | 2.5550000 | 2.5550000 | 2.5550000 |
| CYCLOPENTASILOXANE | 2.1250000 | 2.1250000 | 2.1250000 | 2.1250000 | 2.1250000 | 2.1250000 |
| XANTHAN GUM NF | 1.5000000 | 1.5000000 | 1.5000000 | 1.5000000 | 1.5000000 | 1.5000000 |
| DIMETHICONOL | 0.3750000 | 0.3750000 | 0.3750000 | 0.3750000 | 0.3750000 | 0.3750000 |
| SODIUM HYDROXIDE | 0.1000000 | 0.1000000 | 0.1000000 | 0.1000000 | 0.1000000 | 0.1000000 |
| PROPYLENE GLYCOL | 0.0004850 | 0.0004850 | 0.0048500 | 0.0048500 | 0.0001056 | 0.0001056 |
| METHYLCHLOROISOTHIAZOLINONE | 0.0008050 | 0.0008050 | 0.0008050 | 0.0008050 | 0.0008050 | 0.0008050 |
| METHYLISOTHIAZOLINONE | 0.0002450 | 0.0002450 | 0.0002450 | 0.0002450 | 0.0002450 | 0.0002450 |
| MALIC ACID | 0.0050000 | 0.0050000 | 0.0050000 | 0.0050000 | 0.0050000 | 0.0050000 |
| PANTHENOL | | | | | 0.0005000 | 0.0005000 |
| *HELIANTHUS ANNUUS* (SUNFLOWER) SEED OIL | | | | | 0.0010000 | |
| TOCOPHERYL ACETATE USP/FCC | | | | | | 0.0010000 |
| HYDROXYPROPYLTRIMONIUM HONEY | | | | | | 0.0010000 |
| *TRITICUM VULGARE* (WHEAT) GERM OIL | | | | | | 0.0010000 |
| PEARL POWDER | 0.0010000 | 0.0010000 | | | | |
| *HELIANTHUS ANNUUS* (SUNFLOWER) SEED EXTRACT | | | | | 0.0000034 | |
| *CITRUS MEDICA LIMONUM* (LEMON) PEEL EXTRACT | | | | | 0.0000033 | |
| *CHAMOMILLA RECUTITA* (*MATRICARIA*) FLOWER EXTRACT | | | | | 0.0000033 | |
| HONEY EXTRACT | | | | | | 0.0000050 |
| *TRITICUM VULGARE* (WHEAT) GERM EXTRACT | | | | | | 0.0000050 |
| *CAMELLIA SINENSIS* LEAF EXTRACT | | 0.0001000 | | | | |
| *THEOBROMA CACAO* (COCOA) EXTRACT | 0.0000100 | | | | | |
| ALCOHOL | | | 0.0003300 | 0.0003300 | | |
| LECITHIN | | | 0.0010000 | 0.0010000 | | |
| TOCOPHERYL ACETATE | | | 0.0002600 | 0.0002600 | | |
| MAGNESIUM ASCORBYL PHOSPHATE | | | 0.0002000 | 0.0002000 | | |

-continued

|  | Shade | | | | | |
|---|---|---|---|---|---|---|
| Material Description | I<br>Chestnut<br>% Wt./Wt. | II<br>Amber<br>% Wt./Wt. | III<br>Vivid Red<br>% Wt./Wt. | IV<br>Richer Red<br>% Wt./Wt. | V<br>Platinum<br>% Wt./Wt. | VI<br>Honey<br>% Wt./Wt. |
| RETINYL PALMITATE | | | 0.0000500 | 0.0000500 | | |
| *FRAGARIA VESCA* (STRAWBERRY) FRUIT EXTRACT | | | 0.0000500 | 0.0000500 | | |
| *ZINGIBER OFFICINALE* (GINGER) ROOT EXTRACT | | | 0.0000500 | 0.0000500 | | |
| FRAGRANCE | 0.4000000 | 0.4000000 | 0.6000000 | 0.6000000 | 0.4000000 | 0.4000000 |
| MICA | 0.0840000 | 0.0840000 | 0.0735000 | 0.0735000 | 0.1050000 | 0.1050000 |
| TITANIUM DIOXIDE | 0.0060000 | 0.0060000 | | | 0.0450000 | 0.0450000 |
| IRON OXIDES | 0.0600000 | 0.0600000 | 0.0765000 | 0.0765000 | | |
| EXT. VIOLET 2 | 0.0319000 | 0.0217000 | | 0.0086000 | 0.0001100 | 0.0006600 |
| YELLOW 10 | 0.0098000 | 0.0067000 | | | 0.0002300 | 0.0010700 |
| ORANGE 4 | 0.0336000 | 0.0234000 | 0.0214000 | 0.0233000 | 0.0004700 | 0.0021800 |
| RED 33 | | | 0.0084000 | 0.0058000 | | |

Additional formulations are set forth in the following table.

|  | INCI | | | | | |
|---|---|---|---|---|---|---|
| Material Description | Platinum<br>% wt./wt. | Honey<br>% wt./wt. | Amber<br>% wt./wt. | Chestnut<br>% wt./wt. | Brighter<br>Vivid Red<br>% wt./wt. | Richer Red<br>% wt./wt. |
| WATER | 66.9365244 | 66.9314244 | 66.8855650 | 66.8621550 | 66.7023600 | 66.6944600 |
| PROPYLENE CARBONATE | 15.0000000 | 15.0000000 | 15.0000000 | 15.0000000 | 15.0000000 | 15.0000000 |
| ALCOHOL DENAT. | 4.9500000 | 4.9500000 | 4.9500000 | 4.9500000 | 4.9500000 | 4.9500000 |
| CITRIC ACID | 2.5550000 | 2.5550000 | 2.5550000 | 2.5550000 | 2.5550000 | 2.5550000 |
| PEG-12 DIMETHICONE | 2.4000000 | 2.4000000 | 2.4000000 | 2.4000000 | 2.4000000 | 2.4000000 |
| DIMETHICONE | 2.6400000 | 2.6400000 | 2.6400000 | 2.6400000 | 2.6400000 | 2.6400000 |
| HYDROGENATED POLYDECENE | 2.0000000 | 2.0000000 | 2.0000000 | 2.0000000 | 2.0000000 | 2.0000000 |
| XANTHAN GUM NF | 1.5000000 | 1.5000000 | 1.5000000 | 1.5000000 | 1.5000000 | 1.5000000 |
| OLEYL ALCOHOL | 1.0000000 | 1.0000000 | 1.0000000 | 1.0000000 | 1.0000000 | 1.0000000 |
| DIMETHICONOL | 0.3600000 | 0.3600000 | 0.3600000 | 0.3600000 | 0.3600000 | 0.3600000 |
| SODIUM HYDROXIDE | 0.1000000 | 0.1000000 | 0.1000000 | 0.1000000 | 0.1000000 | 0.1000000 |
| PROPYLENE GLYCOL | 0.0001056 | 0.0001056 | 0.0004850 | 0.0004850 | 0.0048500 | 0.0048500 |
| METHYLCHLOROISOTHIAZOLINONE | 0.0008050 | 0.0008050 | 0.0008050 | 0.0008050 | 0.0008050 | 0.0008050 |
| METHYLISOTHIAZOLINONE | 0.0002450 | 0.0002450 | 0.0002450 | 0.0002450 | 0.0002450 | 0.0002450 |
| MALIC ACID | 0.0050000 | 0.0050000 | 0.0050000 | 0.0050000 | 0.0050000 | 0.0050000 |
| PANTHENOL | 0.0005000 | 0.0005000 | | | | |
| *HELIANTHUS ANNUUS* (SUNFLOWER) SEED OIL | 0.0010000 | | | | | |
| TOCOPHERYL ACETATE USP/FCC | | 0.0010000 | | | | |
| HYDROXYPROPYLTRIMONIUM HONEY | | 0.0010000 | | | | |
| *TRITICUM VULGARE* (WHEAT) GERM OIL | | 0.0010000 | | | | |
| PEARL POWDER | | | 0.0010000 | 0.0010000 | | |
| *HELIANTHUS ANNUUS* (SUNFLOWER) SEED EXTRACT | 0.0000034 | | | | | |
| *CITRUS MEDICA LIMONUM* (LEMON) PEEL EXTRACT | 0.0000033 | | | | | |
| *CHAMOMILLA RECUTITA* (*MATRICARIA*) FLOWER EXTRACT | 0.0000033 | | | | | |
| HONEY EXTRACT | | 0.0000050 | | | | |
| *TRITICUM VULGARE* (WHEAT) GERM EXTRACT | | 0.0000050 | | | | |
| *CAMELLIA SINENSIS* LEAF EXTRACT | | | 0.0001000 | | | |
| *THEOBROMA CACAO* (COCOA) EXTRACT | | | | 0.0000100 | | |
| ALCOHOL | | | | | 0.0003300 | 0.0003300 |
| LECITHIN | | | | | 0.0010000 | 0.0010000 |
| TOCOPHERYL ACETATE | | | | | 0.0002600 | 0.0002600 |
| MAGNESIUM ASCORBYL PHOSPHATE | | | | | 0.0002000 | 0.0002000 |
| RETINYL PALMITATE | | | | | 0.0000500 | 0.0000500 |
| *FRAGARIA VESCA* (STRAWBERRY) FRUIT EXTRACT | | | | | 0.0000500 | 0.0000500 |
| *ZINGIBER OFFICINALE* (GINGER) ROOT EXTRACT | | | | | 0.0000500 | 0.0000500 |

-continued

| | INCI | | | | | |
|---|---|---|---|---|---|---|
| Material Description | Platinum % wt./wt. | Honey % wt./wt. | Amber % wt./wt. | Chestnut % wt./wt. | Brighter Vivid Red % wt./wt. | Richer Red % wt./wt. |
| FRAGRANCE | 0.4000000 | 0.4000000 | 0.4000000 | 0.4000000 | 0.6000000 | 0.6000000 |
| MICA | 0.1050000 | 0.1050000 | 0.0840000 | 0.0840000 | 0.0735000 | 0.0735000 |
| TITANIUM DIOXIDE | 0.0450000 | 0.0450000 | 0.0060000 | 0.0060000 | | |
| IRON OXIDES | | | 0.0600000 | 0.0600000 | 0.0765000 | 0.0765000 |
| EXT. VIOLET 2 | 0.0001100 | 0.0006600 | 0.0217000 | 0.0319000 | | 0.0086000 |
| YELLOW 10 | 0.0002300 | 0.0010700 | 0.0067000 | 0.0098000 | | |
| ORANGE 4 | 0.0004700 | 0.0021800 | 0.0234000 | 0.0336000 | 0.0214000 | 0.0233000 |
| RED 33 | | | | | 0.0084000 | 0.0058000 |

Generalized formulation ranges are set forth in the following table.

| FUNCTION | May include: INCI | FUNCTIONAL RANGE |
|---|---|---|
| Organic Solvent | PROPYLENE CARBONATE<br>ALCOHOL DENAT.<br>ALCOHOL | 1-50% |
| Oil Phase | CYCLOPENTASILOXANE<br>DIMETHICONOL<br>PEG-12 DIMETHICONE<br>DIMETHICONE<br>HYDROGENATED POLYDECENE<br>OLEYL ALCOHOL<br>TOCOPHERYL ACETATE USP/FCC<br>*TRITICUM VULGARE* (WHEAT) GERM OIL<br>*HELIANTHUS ANNUUS* (SUNFLOWER) SEED OIL<br>TOCOPHERYL ACETATE USP/FCC<br>RETINYL PALMITATE<br>FRAGRANCE | 1-30% |
| Hair dye composition | EXT. VIOLET 2<br>YELLOW 10<br>ORANGE 4<br>RED 33 | The acid dyes may be used either singly or in any combination thereof. They may be incorporated in a proportion of 0.001-5% by weight (hereinafter indicated merely by "%"), particularly 0.005-4%, more particularly 0.2-3% based on the total weight of the composition |
| Buffer/Acid system | CITRIC ACID<br>SODIUM HYDROXIDE<br>MALIC ACID | pH of 2-6 |
| Excipient | WATER<br>XANTHAN GUM NF<br>PROPYLENE GLYCOL<br>METHYLCHLOROISOTHIAZOLINONE<br>METHYLISOTHIAZOLINONE<br>PANTHENOL<br>HYDROXYPROPYLTRIMONIUM HONEY<br>PEARL POWDER<br>*HELIANTHUS ANNUUS* (SUNFLOWER) SEED EXTRACT<br>*CITRUS MEDICA LIMONUM* (LEMON) PEEL EXTRACT<br>*CHAMOMILLA RECUTITA* (*MATRICARIA*) FLOWER EXTRACT<br>HONEY EXTRACT<br>*TRITICUM VULGARE* (WHEAT) GERM EXTRACT<br>*CAMELLIA SINENSIS* LEAF EXTRACT<br>*THEOBROMA CACAO* (COCOA) EXTRACT<br>LECITHIN<br>MAGNESIUM ASCORBYL PHOSPHATE<br>*FRAGARIA VESCA* (STRAWBERRY) FRUIT EXTRACT<br>*ZINGIBER OFFICINALE* (GINGER) ROOT EXTRACT<br>MICA<br>TITANIUM DIOXIDE<br>IRON OXIDES | The amounts and each of the one or more ingredients can be varied to achieve desired characteristics for the composition. |

The composition may contain one or more of the above listed solvents in an amount of 1 to 50 percent by weight based on the total weight of the composition. The composition may also contain one or more of the above listed non-aqueous components in an amount of 1 to 30 percent by weight based on the total weight of the composition. The acid dyes may be used either singly or in any combination thereof. They may be incorporated in an amount of 0.001-5% by weight, particularly 0.005-4% by weight, more particularly 0.2-3% by weight, based on the total weight of the composition. The composition may contain a buffer/acid system comprising one or more of citric acid, malic acid and sodium hydroxide to achieve a pH of 2 to 6 for the composition. The composition may also contain water and one or more of the other above listed excipient ingredients. The amounts of each of the one or more excipient ingredients can be varied to achieve desired characteristics for the composition.

Compositions and methods of treating the skin are also provided. The compositions can be aqueous compositions which include one or more acid direct dyes and an organic solvent. The compositions impart a color tone to the skin. The color tone imparted to the skin withstands rinsing. A method is provided which comprises applying an aqueous composition comprising one or more acid direct dyes and an organic solvent to skin, wherein the composition has a pH of 2-6.

According to some embodiments, the compositions further comprise a non-ionic surfactant (e.g., polysorbate-20).

According to some embodiments, the solvent is benzyl alcohol.

Examples of the acid direct dye include Yellow No. 203 (D & C Yellow No. 10, Color Index (CI) given as (CI 47005)), Orange No. 205 (D & C Orange No. 4 (CI 15510)), Red No. 227 (D & C Red No. 33 (CI (Color index) 17200)), D & C Red No. 4, Violet No. 401 (Ext. D & C Violet No. 2 (CI 607301)) and Black No. 401 (CI 20470). According to some embodiments, the compositions include an acid direct dye or a combination of acid direct dyes selected from the group consisting of Yellow No. 10, Orange No. 4, External Violet No. 2, Red No. 4, Red No. 33 and combinations thereof.

The compositions have an acidic pH. For example, the compositions can have a pH of 2 to 6, particularly a pH of 3 to 5, and more particularly a pH of 3.4 to 4.6. For example, the compositions can have a pH of 3.5, 4 or 4.5. The adjustment of the pH may be conducted in accordance with any known method.

The compositions may also include an inorganic base such as sodium hydroxide as well as an organic carboxylic acid. Exemplary organic carboxylic acids include citric acid, malic acid and combinations thereof.

The compositions can also include a fragrance.

The composition can be applied to the skin (e.g., via spraying). According to some embodiments, the composition can be in the form of an aerosol. The composition can be applied multiple times to achieve darker skin tones. According to some embodiments, the composition is not rinsed from the skin after application.

According to some embodiments, the composition is free of anionic surfactants.

Alternatively, the composition can be applied to the skin, allowed to remain in contact with the skin for a period of time and subsequently rinsed from the skin. For example, the composition can be in the form of a body wash. According to some embodiments, the composition can be rinsed from the skin after being allowed to remain in contact with the skin for 30 seconds or more (e.g., at least 60 seconds). According to some embodiments, the composition can include one or more anionic surfactants.

An exemplary composition for application to the skin is provided in the following Table.

| Part | INCI Name (% activity) | w/w % | Target |
|------|------------------------|-------|--------|
| A | Deionized water | 9.1003% | 364.012 |
| B | Deionized Water | 89.6500% | 3586.000 |
|   | Lactic Acid 88% | 0.0570% | 2.280 |
|   | Malic Acid 50% | 0.1000% | 4.000 |
| C | Benzyl alcohol | 0.3000% | 12.000 |
|   | Polysorbate-20 | 0.2400% | 9.600 |
|   | Starglow Fragrance | 0.0800% | 3.200 |
|   | EXT Violet 2 | 0.0065% | 0.260 |
| C-2 | Benzyl alcohol | 0.1000% | 4.000 |
| D | Red 4 | 0.0016% | 0.064 |
|   | Yellow 10 | 0.0059% | 0.234 |
|   | Orange 4 | 0.0088% | 0.350 |
| E | DMDM Hydantoin | 0.3000% | 12.000 |
|   | Sodium Hydroxide 50% = pH 4.0 | 0.0500% | 2.000 |
|   | subtotal | 100.0000% | 4000.00 |

The composition can be made by the following process:

Add Part B to Part A with mixing. Premix Part C separately until uniform. Add Part C to the mixture of parts A and B. Add C-2 to the mixture of parts A, B and C. Weigh out Part D and add components one at a time to the mixture of parts A, B, C and C-2 with mixing until uniform. Add part E to the mixture of parts A, B, C, C-2 and D while mixing until uniform.

Two exemplary formulations were evaluated. Formulation 1 had a composition as set forth in the above table except that the benzyl alcohol and Violet 2 dye were not included in part C of Formulation 1. Formulation 2 had a composition identical to that given in the table. The formulations were tested on the skin of an end-user. Skin tone was measured using a Minolta Chromameter. The following testing protocol was used.

1) take initial LAB measurements 2) apply test solution to the skin for 60 seconds and take LAB measurements 3) rinse for 15 seconds and take LAB measurements; take digital pictures 4) following SGL wash protocol, wash each test location, then take LAB measurements; take digital pictures.

The following Table shows the baseline measurement before application of the composition to the skin.

| Baseline | |
|---|---|
| Formulation | |
| 1 | 2 |
| pH | |
| 4.0 | 4.0 |
| 60 Sec | 60 Sec |
| 66.91 | 68.73 |

The following Table shows the chromameter data for skin tone after one 60 second application of the compositions to the skin.

| 1 Use | | |
|---|---|---|
| | Formulation | |
| | 1 | 2 |
| | pH | |
| | 4.0 | 4.0 |
| | 60 Sec | 60 Sec |
| Before rinse | 60.67 | 60.77 |
| After rinse | 61.10 | 61.44 |
| Before wash | 61.10 | 61.44 |
| After wash | 64.09 | 64.97 |

The following Table shows the change in skin tone as measured by chromameter from baseline before rinsing, after rinsing, before washing and after washing. The difference in skin tone before and after rinsing and before and after washing is also provided.

| 1 Use ΔL* | | |
|---|---|---|
| | Formulation | |
| | 1 | 2 |
| | pH | |
| | 4.0 | 4.0 |
| Panelist | 60 Sec | 60 Sec |
| Before rinse | −6.24 | −7.96 |
| After rinse | −5.81 | −7.29 |
| Before wash | −5.81 | −7.29 |
| After wash | −2.82 | −3.76 |
| B4/Aft rinse | −0.43 | −0.67 |
| B4/Aft wash | −2.99 | −3.53 |

The following Table shows the change in skin tone from baseline before rinsing, after rinsing, before washing and after washing for one use.

| Darkness - Change from Baseline | | | | | | | |
|---|---|---|---|---|---|---|---|
| Formulation | pH | time | Base | Before rinse | After rinse | Before wash | After wash |
| 1 | 4.0 | 60 Sec | 0 | −6.24 | −5.81 | −5.81 | −2.82 |
| 2 | 4.0 | 60 Sec | 0 | −7.96 | −7.29 | −7.29 | −3.76 |

The data in the above table is depicted in the graph of FIG. 1. As can be seen from FIG. 1, the skin tone becomes significantly darker upon application of the compositions to the skin for 60 seconds. The skin tone remains significantly darker even after rinsing and washing.

While the foregoing specification teaches the principles of the present invention, with examples provided for the purpose of illustration, it will be appreciated by one skilled in the art from reading this disclosure that various changes in form and detail can be made without departing from the true scope of the invention.

What is claimed is:

1. A method comprising:
    applying an aqueous composition comprising one or more acid direct dyes selected from the group consisting of Violet 2, Red 4, Yellow 10, Organic 4, Red 33 and combination thereof and an organic solvent benzyl alcohol to skin, wherein the composition has a pH of 2-6, and wherein said composition is free of anionic surfactants.

2. The method of claim 1, wherein the composition further comprises a carboxylic acid compound selected from the group consisting of lactic acid, citric acid, malic acid and combinations thereof.

3. The method of claim 1, wherein the composition further comprises a non-ionic surfactant.

4. The method of claim 3, wherein the non-ionic surfactant is polysorbate-20.

5. The method of claim 1, wherein the composition has a pH of 3 to 5.

6. The method of claim 1, wherein the composition is applied to the skin by spraying.

7. The method of claim 6, wherein the composition is an aerosol.

8. The method of claim 1, wherein the composition is not rinsed from the skin after application thereto.

9. The method of claim 1, further comprising rinsing the composition from the skin with water.

10. The method of claim 9, wherein the composition is rinsed from the skin 30 seconds or more after applying.

11. The method of claim 1, wherein the composition has a pH of 3.4 to 4.6.

12. The method of claim 9, wherein the composition is rinsed from the skin 60 seconds or more after applying.

13. The method of claim 1, wherein the one or more acid direct dyes consist of Violet 2, Red 4, Yellow 10 and Orange 4.

14. The method of claim 1, wherein the one or more acid direct dyes consist of Red 4, Yellow 10 and Orange 4.

15. The method of claim 1, wherein the skin tone becomes darker upon application to the skin and wherein the skin tone remains darker after rinsing and washing the skin.

* * * * *